United States Patent
Bi et al.

(10) Patent No.: US 12,214,057 B2
(45) Date of Patent: Feb. 4, 2025

(54) GRAPHENE QUANTUM DOTS-GADOLINIUM ION CHELATE AS MAGNETIC RESONANCE IMAGING CONTRAST AGENT AND PREPARATION METHOD THEREOF

(71) Applicant: ANHUI UNIVERSITY, Hefei (CN)

(72) Inventors: Hong Bi, Hefei (CN); Dong Wang, Hefei (CN)

(73) Assignee: ANHUI UNIVERSITY, Hefei (CN)

( * ) Notice: Subject to any disclaimer, the term of this patent is extended or adjusted under 35 U.S.C. 154(b) by 769 days.

(21) Appl. No.: 17/422,211

(22) PCT Filed: Mar. 5, 2019

(86) PCT No.: PCT/CN2019/076939
§ 371 (c)(1),
(2) Date: Jul. 12, 2021

(87) PCT Pub. No.: WO2020/155286
PCT Pub. Date: Aug. 6, 2020

(65) Prior Publication Data
US 2022/0072161 A1 Mar. 10, 2022

(30) Foreign Application Priority Data

Jan. 31, 2019 (CN) .......................... 201910095524.6

(51) Int. Cl.
| | | |
|---|---|---|
| A61K 49/00 | (2006.01) |
| A61K 49/08 | (2006.01) |
| B82Y 5/00 | (2011.01) |
| B82Y 20/00 | (2011.01) |
| B82Y 30/00 | (2011.01) |
| B82Y 40/00 | (2011.01) |
| C01B 32/198 | (2017.01) |
| C09K 11/65 | (2006.01) |

(52) U.S. Cl.
CPC ...... *A61K 49/0002* (2013.01); *A61K 49/0019* (2013.01); *A61K 49/085* (2013.01); *C01B 32/198* (2017.08); *C09K 11/65* (2013.01); *B82Y 5/00* (2013.01); *B82Y 20/00* (2013.01); *B82Y 30/00* (2013.01); *B82Y 40/00* (2013.01); *C01P 2004/04* (2013.01); *C01P 2004/64* (2013.01); *C01P 2004/80* (2013.01); *C01P 2006/60* (2013.01); *C01P 2006/82* (2013.01)

(58) Field of Classification Search
None
See application file for complete search history.

(56) References Cited

U.S. PATENT DOCUMENTS

2015/0340171 A1* 11/2015 Li .................. C01B 32/192
524/379

FOREIGN PATENT DOCUMENTS

| CN | 102397563 A | | 4/2012 |
| CN | 103143361 A | * | 6/2013 |
| CN | 103330950 A | * | 10/2013 |
| CN | 103708446 A | | 4/2014 |
| CN | 105797174 A | | 7/2016 |
| CN | 106348281 A | | 1/2017 |

OTHER PUBLICATIONS

Chen et al. (Gadolinium-encapsulated graphene carbon nanotheranostics for imaging-guided photodynamic therapy, Jul. 23, 2018, Advanced Materials) (Year: 2018).*
Sukhanova et al. (Controlled Self-Assembly of Nanocrystals into Polycrystalline Fluorescent Dendrites with Energy-Transfer Properties, Mar. 13, 2006, Anegwandte Chemie International Edition, 45:13) (Year: 2006).*
Gedda et al. (Facile synthesis of gold/gadolinium-doped carbon quantum dot nanocomposites for magnetic resonance imaging and photothermal ablation therapy, Jul. 7, 2017, Journal of Materials Chemistry B, 5:6282) (Year: 2017).*
Ha (Upconversion photoluminescent metal ion sensors via two photon absorption in graphene oxide quantum dots, Oct. 2, 2014, Carbon, 81:367-375) (Year: 2014).*

(Continued)

*Primary Examiner* — Johann R Richter
*Assistant Examiner* — Kaila A Craig
(74) *Attorney, Agent, or Firm* — Bayramoglu Law Offices LLC

(57) ABSTRACT

A graphene quantum dots-gadolinium ion chelate (Gd@GQDs) nanomaterial with hydrophilic groups on the surface has a preparation method that includes: preparing graphene oxide by using a Hummers method; subsequently, subjecting the graphene oxide to heating, oxidation, and purification to obtain pure graphene quantum dots; and finally, chelating the graphene quantum dots with $Gd^{3+}$ to form stable Gd@GQDs. The Gd@GQDs is easily dispersed in water, phosphate buffered solution (PBS), biological medium and other aqueous system, has good biocompatibility and low cytotoxicity, shows an excellent $T_1$-weighted contrast performance in a 1.5-Tesla magnetic resonance testing system, and has a relaxation rate $r_1$ as high as 72 $mM^{-1}s^{-1}$, the value of $r_1$ being 20 times higher than that of the current commercial $T_1$-weighted magnetic resonance imaging contrast agent Gd-DTPA.

15 Claims, 3 Drawing Sheets

(56) References Cited

OTHER PUBLICATIONS

Shi (Facile synthesis of gadolinium (III) chelates functionalized carbon quantum dots for fluorescence and magnetic resonance dual-modal bioimaging, Jun. 4, 2015, Carbon, 93:742-750) (Year: 2015).*
Daniela C. Marcano, et al., Improved Synthesis of Graphene Oxide, ACS NANO, 2010, pp. 4806-4814, vol. 4 No. 8.
Hongmin Chen, et al., Gd-Encapsulated Carbonaceous Dots with Efficient Renal Clearance for Magnetic Resonance Imaging, Adv. Mater., 2014, pp. 6761-6766, 26.
Hongmin Chen, et al., Gadolinium-Encapsulated Graphene Carbon Nanotheranostics for Imaging-Guided Photodynamic Therapy, Adv. Mater., 2018, pp. 1802748(1-9), 30.

\* cited by examiner

GRAPHENE QUANTUM DOTS-GADOLINIUM ION CHELATE AS MAGNETIC RESONANCE IMAGING CONTRAST AGENT AND PREPARATION METHOD THEREOF

CROSS REFERENCE TO THE RELATED APPLICATIONS

This application is the national phase entry of International Application No. PCT/CN2019/076939, filed on Mar. 5, 2019, which is based upon and claims priority to Chinese Patent Application No. 201910095524.6, filed on Jan. 31, 2019, the entire contents of which are incorporated herein by reference.

TECHNICAL FIELD

The present invention belongs to the technical field of nanomaterials and nanotechnology, and specifically, relates to a graphene quantum dots-gadolinium ion chelate as a magnetic resonance imaging contrast agent and a preparation method thereof.

BACKGROUND

Magnetic resonance imaging (MRI) is one of the most widely used diagnostic tools in clinical applications. MRI has advantages of non-invasiveness, high spatial and temporal resolution, and good soft-tissue contrast. Nevertheless, the inherent signal differences between tissues, especially the difference between diseased and normal tissues, are not that great. Therefore, generally, MRI contrast agents are injected before scanning to improve imaging quality. According to the principle of action, MRI contrast agents can be divided into longitudinal relaxation contrast agents ($T_1$ contrast agents) and transverse relaxation contrast agents ($T_2$ contrast agents). The most commonly used $T_1$ contrast agent is a gadolinium-based contrast agent. Gadolinium ion ($Gd^{3+}$) can provide seven unpaired electrons, resulting in a higher longitudinal relaxation rate ($r_1$). However, free $Gd^{3+}$ is highly toxic. $Gd^{3+}$ can induce a rare disease called nephrogenic systemic fibrosis (NSF) in vivo, which is particularly fatal in patients with impaired renal function. In order to inhibit the cytotoxicity of $Gd^{3+}$, various ligands are usually used to chelate with $Gd^{3+}$ to minimize free $Gd^{3+}$ leakage. Examples of $Gd^{3+}$ chelates include Gd-diethylene triamine pentaacetic acid (Gd-DTPA), gadoteric acid, Gd-1,4,7-tris(carboxymethylaza)cyclododecane-10-azaacetylamide butrol (Gd-DO3A butrol), gadodiamide (Gd-DTPA-BMA) and others. However, the gadolinium content and actual dosage of these gadolinium-based chelates are substantially high, which still leads to the $Gd^{3+}$ leakage in the body and causes biological safety problems. Therefore, the development of $T_1$-weighted contrast agents with extremely low $Gd^{3+}$ content, good biosafety and high performance are urgently desirable.

Graphene quantum dots (GQDs) are mainly composed of $sp^2$-hybridized carbon atoms, have the same lattice spacing as graphite, and are two-dimensional graphene sheets with lateral dimensions less than 100 nm and atomic layers less than 10 layers. GQDs not only have the excellent properties of graphene, such as large specific surface area, high electron mobility and good mechanical strength, but also have the good properties of excellent fluorescence property and photostability, low cytotoxicity, good biocompatibility and easy surface modification. Because of these excellent properties, GQDs have great application prospects in the fields of biomedical imaging, optical materials and devices, biosensing and environmental detection, especially providing a material basis for the construction of multi-modal imaging platforms for clinical applications.

With the urgent need for early diagnosis and precise treatment of major diseases such as cancer, single diagnostic techniques such as MRI, fluorescence imaging and ultrasound imaging have been unable to meet the needs of people. Therefore, the multi-mode imaging technology and materials thereof, which integrate multiple functions, have received extensive attention and research from scientific researchers. In view of the above-mentioned problems, the present invention provides a GQDs-gadolinium ion chelate with MRI and fluorescence imaging functions as a medical imaging agent.

The prior art related to the present invention is introduced as follows. The literature on using a composite of carbon quantum dots and gadolinium as an MRI contrast agent has been published in the international academic journals *Advanced Materials* 2014, 26, 6761-6766 and *Advanced Materials* 2018, 1802748. The composite of carbon quantum dots and gadolinium was synthesized by chelating small organic molecules and gadolinium ions, or synthesized via hydro/solvothermal method using commercial gadolinium-based contrast agents, and then used for MRI. The disadvantages of this method are that the raw materials are expensive, the structure of the obtained composite of carbon quantum dots and gadolinium is not very clear, and the gadolinium content and the amount used for imaging are high, which will have a great impact on the organism in the later stage. More importantly, the longitudinal relaxation rate $r_1$ of the contrast agent is much smaller than that of the contrast agent of the present invention, so its $T_1$-weighted contrast effect is far inferior to that of the claimed technology of the present invention.

SUMMARY

In view of the above-mentioned defects in the prior art, the present invention provides a graphene quantum dots-gadolinium ion chelate with good biocompatibility and low cytotoxicity, which can be applied to MRI and fluorescence imaging, and has excellent $T_1$-weighted contrast effect and high-efficiency fluorescence function.

The present invention further provides a preparation method and an application of the graphene quantum dots-gadolinium ion chelate.

In order to achieve the above objective, the present invention provides a graphene quantum dots-gadolinium ion chelate. The graphene quantum dots-gadolinium ion chelate is a nanomaterial with a large specific surface area, stable optical properties, and hydrophilic groups on the surface.

In addition, the present invention further provides a method for preparing the graphene quantum dots-gadolinium ion chelate, including: preparing graphene oxide by using a Hummers method; subsequently, subjecting the graphene oxide to heating and oxidation to obtain pure graphene quantum dots; and finally, chelating the graphene quantum dots with $Gd^{3+}$ to form the stable graphene quantum dots-gadolinium ion chelate.

As an improvement, the method specifically includes the following steps:
1) preparing the graphene oxide by using the Hummers method;
2) weighing and dissolving the prepared graphene oxide in deionized water, performing ultrasonic treatment, and adding a certain amount of a strong oxidant for being fully dissolved to obtain a solution;

3) adding 400-1,000 μL of a basic compound to the solution, and then refluxing for 7-12 h at 70-120° C.;

4) after the refluxing is completed, performing purification and drying to obtain the graphene quantum dots, and the graphene quantum dots have the characteristics of two-dimensional regular morphology, a uniform size, a lateral dimension ranging from 3 nm to 6 nm, a thickness ranging from 1 nm to 2 nm, and excitation-independent fluorescence;

5) preparing the pure graphene quantum dots into a solution with a certain concentration, and then adding a certain amount of a gadolinium chloride solution to perform a chelation reaction under certain conditions to obtain a solution after the reaction; and 6) performing purification and drying on the solution after the reaction to obtain the graphene quantum dots-gadolinium ion chelate.

As an improvement, an ultrasonic power in the step 2) is 500-800 W.

As an improvement, the strong oxidant in step 2) is a mixture of one or more of potassium persulfate, hydrogen peroxide, concentrated sulfuric acid, concentrated nitric acid, and hypochloric acid.

As an improvement, in step 2), a mass ratio of the graphene oxide to the strong oxidant is (1-3):(1,000-3,000); a mass ratio of the graphene oxide to the deionized water is (1-3):(1,000-3,000).

As an improvement, the basic compound in step 3) is a mixture of one or more of potassium hydroxide, sodium hydroxide, ammonia, hydrazine hydrate, ethylenediamine, and hydroxylamine.

As an improvement, the purification in step 4) and step 6) is any one or more methods selected from the group consisting of suction filtration, chromatography, dialysis, filtration, extraction, distillation and fractionation; the drying in step 4) and step 6) is any one or more methods selected from the group consisting of vacuum drying, freeze drying, and high temperature drying.

As an improvement, in step 5), the concentration of the solution prepared by the graphene quantum dots is 0.05-0.4 mg mL$^{-1}$; a concentration of the gadolinium chloride solution is 0.1-0.5 mmol·L$^{-1}$.

As an improvement, the chelation reaction in the step 5) is performed by any one method selected from the group consisting of conventional water bath heating, hydrothermal reaction, solution dialysis, and room temperature treatment, in which the room temperature treatment has a relatively longer time for chelation.

Finally, the present invention further provides an application of the chelate or the graphene quantum dots-gadolinium ion chelate obtained by the preparation method as a medical imaging contrast agent.

As an improvement, the medical imaging contrast agent includes an MRI contrast agent and a fluorescent imaging agent.

Compared with the prior art, the present invention has the advantages as follows.

1) The graphene quantum dots-gadolinium ion chelate (Gd@GQDs) prepared by the present invention is a nano-material with hydrophilic groups such as hydroxyl, carboxyl, and amino groups on the surface. The Gd@GQDs has a uniform size and stable optical properties, and is easy to carry out surface modification.

2) The Gd@GQDs prepared by the present invention is easily dispersed in aqueous systems such as water, phosphate buffered solution (PBS), and biological medium.

3) The cytotoxicity of the Gd@GQDs prepared by the present invention was tested by using 3-(4,5-dimethylthiazol-2-yl)-2,5-diphenyltetrazolium bromide (MTT) assay. The test results showed that after co-incubation of human breast cancer (MCF-7) cells and Chinese hamster ovary (CHO) cells with different concentrations of Gd@GQDs and Dulbecco's modified eagle medium (DMEM) solution for 24 h, the viability of the cells was still maintained above 90%, indicating that the Gd@GQDs prepared by the present invention has very low cytotoxicity.

4) The Gd@GQDs prepared by the present invention further has excellent fluorescence performance, and its fluorescence shows an excitation-independent behavior as that of typical graphene quantum dots.

5) The Gd@GQDs prepared by the present invention exhibits excellent $T_1$-weighted contrast performance in a 1.5-Tesla magnetic resonance test system, and its relaxation rate $r_1$ is as high as 72 mM$^{-1}$s$^{-1}$, which is 5-12 times the $r_1$ of the carbon quantum dots and gadolinium composite contrast agent reported in the above literature, and is also more than 20 times of the $r_1$ value (3.0-4.0 mM$^{-1}$s$^{-1}$) of the existing commercial $T_1$-weighted magnetic resonance imaging contrast agent Gd-DTPA. It is particularly important that in practical applications, the injection dosage of Gd$^{3+}$ in Gd@GQDs is one-fiftieth of that of the gadolinium-based $T_1$ contrast agent in the above-mentioned literature and the general commercial gadolinium-based $T_1$ contrast agent. In addition, although the Gd$^{3+}$ content in the Gd@GQDs material of the present invention is only one quarter to one third of that of the gadolinium-based $T_1$ contrast agent in the above-mentioned literature, it can still achieve a good magnetic resonance imaging effect, which avoids the hidden danger of a large number of Gd$^{3+}$ leakage at source. Therefore, the Gd@GQDs magnetic resonance imaging contrast agent of the present invention has a good application prospect in clinical practice.

BRIEF DESCRIPTION OF THE DRAWINGS

FIGS. 5A-5D are diagrams showing $T_1$-weighted magnetic resonance images of Gd@GQDs prepared by the present invention, GQDs, gadolinium chloride and Gd-DTPA after co-incubated with MCF-7 cells, measured with the 1.5-Tesla magnetic resonance imaging system, wherein FIG. 5A is a diagram showing a $T_1$-weighted magnetic resonance image of GQDs, FIG. 5B is a diagram showing a $T_1$-weighted magnetic resonance image of gadolinium chloride, FIG. 5C is a diagram showing a $T_1$-weighted magnetic resonance image of Gd-DTPA, and FIG. 5D is a diagram showing a $T_1$-weighted magnetic resonance image of Gd@GQDs.

DETAILED DESCRIPTION OF THE EMBODIMENTS

The following embodiments are further descriptions of the contents of the present invention as explanations of the technical contents of the present invention, but the essential content of the present invention is not limited to those described in the embodiments below. Those of ordinary skill in the art can and should be aware that any simple changes or substitutions based on the essential spirit of the present invention should fall within the protective scope claimed by the present invention.

Embodiment 1

A preparation method of a graphene quantum dots-gadolinium ion chelate, specifically including the steps as follows.

1) Graphene oxide is prepared by using a Hummers method (this method is cited from the literature: ACS Nano, 2010, 4 (8), 4806-4814.).

2) 20 mg of the above graphene oxide is weighed, dissolved in 60 g of deionized water, treated with an ultrasonic power of 500 W, and then 60 g of hydrogen peroxide is added and then fully dissolved to obtain a solution.

3) 1,000 μL of a hydrazine hydrate solution is added to the above solution, and then the resulting solution is transferred to a round bottom flask, and refluxed in an oil bath at 100° C. for 8 h.

4) After the reflux reaction, the resulting solution is filtered and purified to remove bulk impurities, and then dried at a temperature of 80° C. to obtain GQDs, and the GQDs have the characteristics of two-dimensional regular morphology, a uniform size, a lateral dimension ranging from 3 nm to 6 nm, a thickness ranging from 1 nm to 2 nm, and excitation-independent fluorescence.

5) The GQDs prepared above are formulated into a solution with a concentration of 0.35 mg mL$^{-1}$, and then gadolinium chloride is added, a concentration of the gadolinium chloride solution is controlled to 0.45 mmol·L$^{-1}$, and a chelation reaction is carried out in a hydrothermal autoclave at 120° C. to obtain a solution after the reaction.

6) The above-mentioned solution after the reaction is subjected to rotary evaporation and a lyophilization treatment to obtain Gd@GQDs.

The performance of Gd@GQDs prepared in Embodiment 1 is tested.

Figure 1:
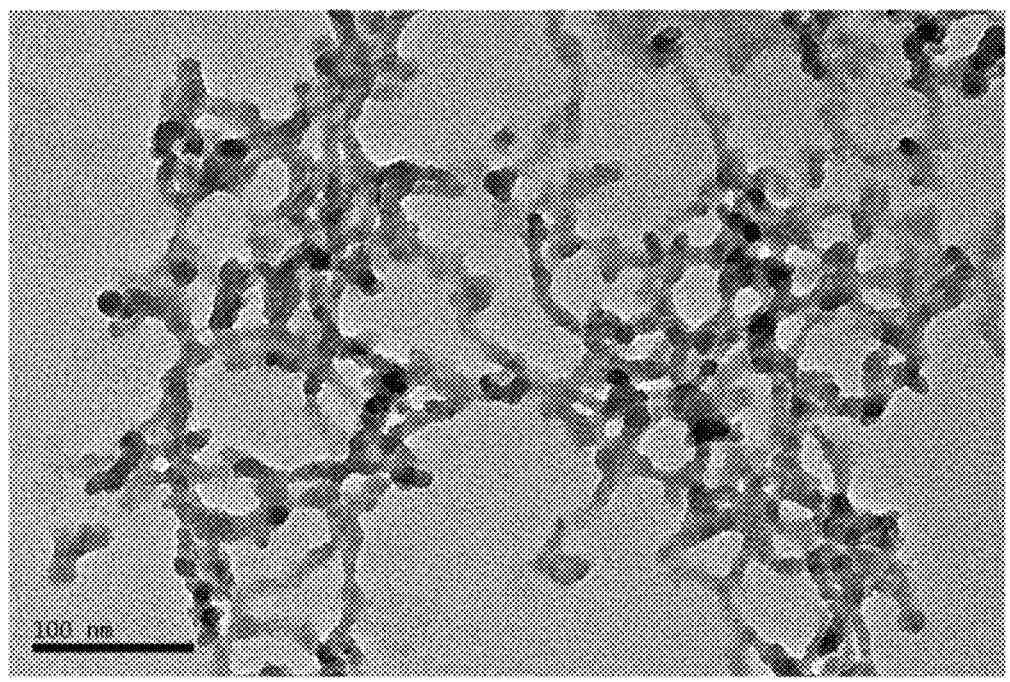
FIG. 1 is a transmission electron microscopy (TEM) image of Gd@GQDs prepared by the present invention.

FIG. 1 is a TEM image of the Gd@GQDs. It can be found that after the addition of gadolinium ions, GQDs exhibit a self-assembly behavior, which has the characteristics of a large specific surface area, stable optical properties, and hydrophilic groups on the surface.

Figure 2:
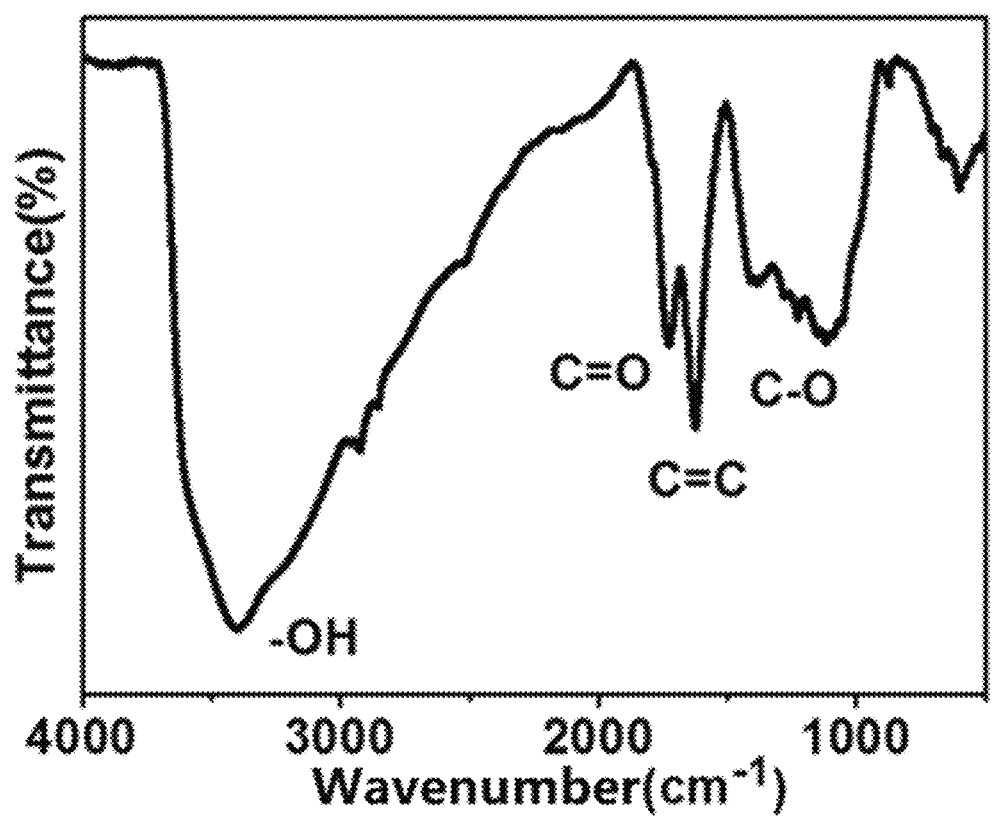
FIG. 2 is a Fourier transform infrared (FT-IR) spectrum of Gd@GQDs prepared by the present invention.

FIG. 2 is an FT-IR spectrum of the Gd@GQDs prepared by the present invention. In the figure, 3398 cm$^{-1}$ is the hydroxyl (O—H) stretching vibration peak, 2948 cm$^{-1}$ is the secondary amino group N—H stretching vibration peak, 1725 cm$^{-1}$ is the C=O asymmetric stretching vibration peak, and 1600 cm$^{-1}$ is the C=C stretching vibration peak, indicating that the Gd@GQDs prepared by the present invention has a large number of hydrophilic groups and maintains a certain graphene structure.

Figure 3:
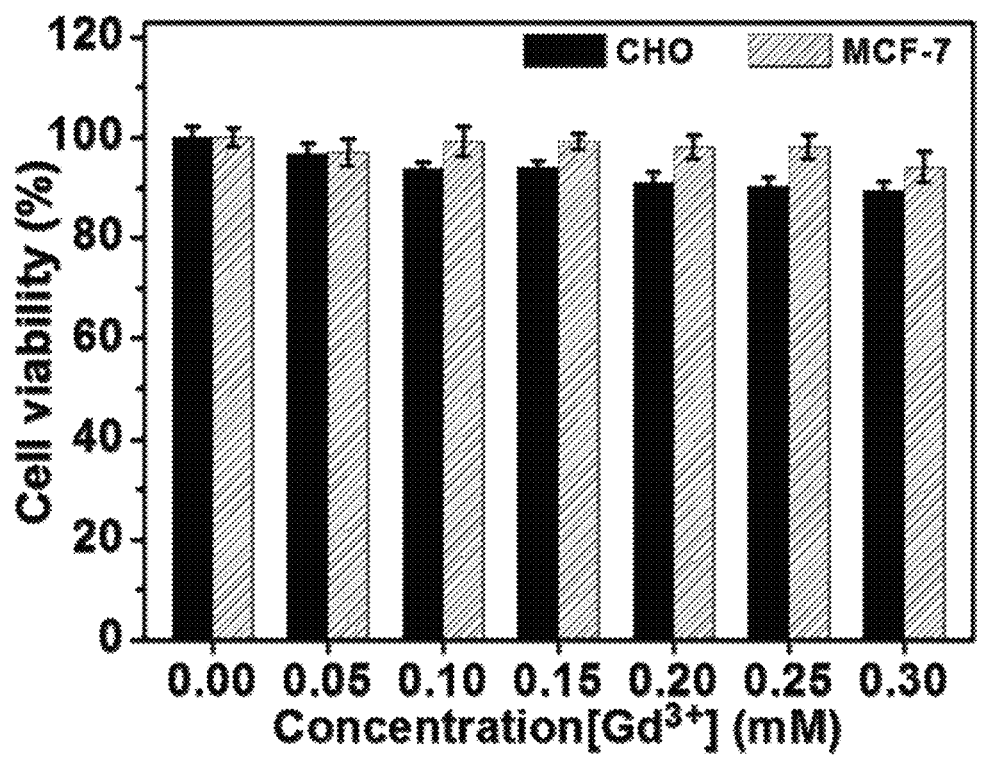
FIG. 3 is a diagram showing cytotoxicity test results by using MTT assay of Gd@GQDs (different concentrations of Gd@GQDs co-incubated with CHO cells and MCF-7 cells for 24 h, respectively) prepared by the present invention.

FIG. 3 is a diagram showing the cytotoxicity of the prepared Gd@GQDs measured by the MTT assay. The MTT assay is a common method for detecting cell viability and growth. The detection principle is that succinate dehydrogenase in the mitochondria of living cells can reduce exogenous MTT (thiazole blue) into water-insoluble blue-purple crystalline formazan that deposits in cells, while dead cells do not have such function. Then, dimethyl sulfoxide (DMSO) is used to dissolve the formazan in the cells, and then its light absorption value is measured by an enzyme-linked immunosorbent reader at a wavelength of 540 nm or 720 nm, which can indirectly reflect the number of living cells.

The cytotoxicity test results by using MTT assay showed that after co-cultivating MCF-7 cells and CHO cells (both provided by the School of Life Sciences, Anhui University) with Gd@GQDs for 24 h, the viability of the cells was still remained above 90%, indicating that the prepared Gd@GQDs has very low cytotoxicity.

Figure 4:
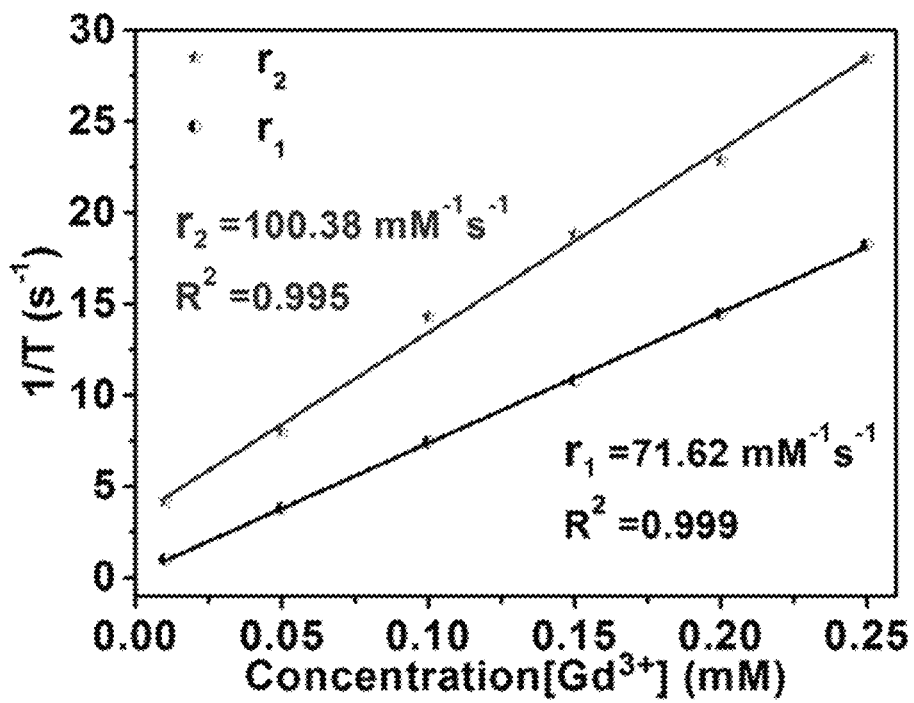
FIG. 4 is a diagram showing relaxation rates $r_1$ and $r_2$ of an aqueous solution of Gd@GQDs prepared by the present invention in a 1.5-Tesla magnetic resonance imaging system ($R^2$ in the figure is a fitting correlation coefficient)
Figure 5A:
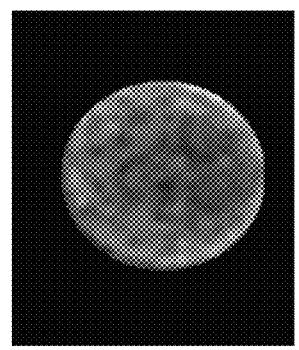
Figure 5B:
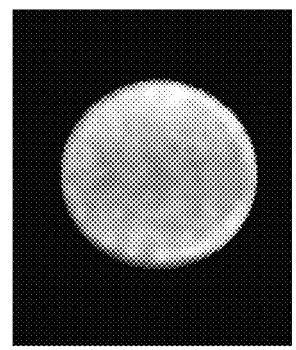
Figure 5C:
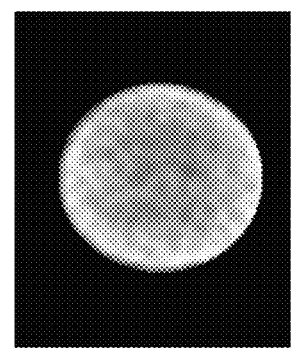
Figure 5D:
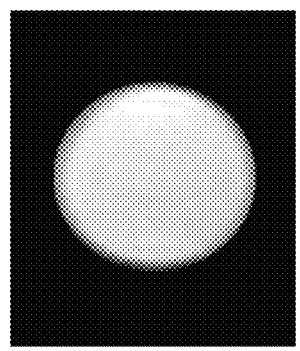

FIG. 4 shows relaxation rates $r_1$ and $r_2$ of Gd@GQDs prepared by the present invention in a 1.5-Tesla MRI system, indicating that Gd@GQDs has an extremely high relaxation rate $r_1$.

FIGS. 5A-5D show $T_1$-weighted magnetic resonance images of Gd@GQDs (0.2 mg·mL$^{-1}$ with a Gd$^{3+}$ content of 0.2 mmol· L$^{-1}$) prepared by the present invention, graphene quantum dots (0.2 mg mL$^{-1}$), gadolinium chloride (0.2 mmol·L$^{-1}$) and Gd-DTPA (0.2 mmol·L$^{-1}$) after co-incubated with MCF-7 cells respectively and measured with the 1.5-Tesla MRI system, showing that Gd@GQDs has an excellent contrast effect in cellular MRI.

Embodiment 2

A preparation method of a graphene quantum dots-gadolinium ion chelate, specifically including the steps as follows.

1) Graphene oxide is prepared by using a Hummers method.

2) 60 mg of the above graphene oxide is weighed, dissolved in 60 g of deionized water, treated with an ultrasonic power of 800 W, and then 60 g of a potassium persulfate solution with a concentration of 1 mol· L$^{-1}$ is added and then fully dissolved to obtain a solution.

3) 800 μL of an ammonia solution is added to the above solution, and then the resulting solution is transferred to a round bottom flask, and refluxed in an oil bath at 70° C. for 12 h.

4) After the reflux reaction, the resulting solution is purified by chromatography to remove bulk impurities, and then freeze-dried to obtain GQDs.

5) The GQDs prepared above are formulated into a solution with a concentration of 0.2 mg·mL$^{-1}$, and then gadolinium chloride is added, a concentration of the gadolinium chloride solution is controlled to 0.2 mmol·L$^{-1}$, and a chelation reaction is carried out at room temperature to obtain a solution after the reaction.

6) The above-mentioned solution after the reaction is dialyzed, and then dried at a temperature of 100° C. to obtain Gd@GQDs.

Embodiment 3

A preparation method of a graphene quantum dots-gadolinium ion chelate, specifically including the steps as follows.

1) Graphene oxide is prepared by using a Hummers method.

2) 60 mg of the above graphene oxide is weighed, dissolved in 60 g of deionized water, treated with an ultrasonic power of 600 W, and then 20 g of a mixture of concentrated sulfuric acid and concentrated nitric acid is added and then fully dissolved to obtain a solution.

3) 400 μL of a 1 mol·L$^{-1}$ sodium hydroxide solution is added to the above solution, and then the resulting solution is transferred to a round bottom flask, and refluxed in an oil bath at 80° C. for 10 h.

4) After the reflux reaction, the resulting solution is subjected to suction filtration and a purification treatment to remove bulk impurities, and then subjected to a vacuum drying treatment to obtain GQDs.

5) The GQDs prepared above are formulated into a solution with a concentration of 0.05 mg mL$^{-1}$, and then gadolinium chloride is added, a concentration of the gadolinium chloride solution is controlled to 0.1 mmol·L$^{-1}$, and a chelation reaction is carried out in a water bath at 60° C. to obtain a solution after the reaction.

6) The above-mentioned solution after the reaction is subjected to distillation and a drying treatment to obtain Gd@GQDs.

The graphene quantum dots-gadolinium ion chelate (Gd@GQDs) prepared by the present invention is used according to the same operation steps as commercial contrast agents. The Gd@GQDs can be used as an MRI contrast agent as well as a fluorescent imaging agent.

The Gd@GQDs prepared by the present invention is easily dispersed in aqueous systems such as water, PBS, and biological medium, has good biocompatibility and low cytotoxicity, shows an excellent $T_1$-weighted contrast performance in a 1.5-Tesla magnetic resonance testing system, and has a relaxation rate $r_1$ as high as 72 mM$^{-1}$s$^{-1}$, the value of $r_1$ being 20 times higher than that of the current commercial $T_1$-weighted MRI contrast agent Gd-DTPA. In practical applications, the injection dosage of Gd$^{3+}$ in Gd@GQDs is one-fiftieth of that of the gadolinium-based $T_1$ contrast agent in the above-mentioned literature and the general commercial gadolinium-based $T_1$ contrast agent. In addition, although the content of Gd$^{3+}$ in the Gd@GQDs material of the present invention is only one quarter to one third of that of the gadolinium-based $T_1$ contrast agent in the above-mentioned literature, it can still achieve a good MRI effect, which avoids the hidden danger of a large number of Gd$^{3+}$ leakage at source. The Gd@GQDs of the present invention can be used as a medical imaging contrast agent, and has a good application prospect in clinical practice.

The foregoing descriptions are merely preferred embodiments of the present invention, which are not used to limit the present invention. Any modifications, equivalent substitutions or improvements within the spirit and principle of the present invention shall all fall within the protective scope of the present invention.

What is claimed is:

1. A method for preparing the graphene quantum dots-gadolinium ion chelate, comprising the following steps:
   1) Preparing graphene oxide by using a Hummers method;
   2) Weighing and dissolving the graphene oxide in deionized water to obtain a first solution, performing an ultrasonic treatment on the first solution, and then adding a predetermined amount of a strong oxidant for being fully dissolved to obtain a second solution, wherein the strong oxidant is a mixture of at least one of potassium persulfate, hydrogen peroxide, and hypochloric acid;
   3) Adding 400-1,000 μL of a basic compound to the second solution to obtain a resulting solution, and then refluxing the resulting solution for 7-12 h at 70-120° C.;
   4) After the resulting solution is refluxed, performing a purification and a drying on the resulting solution to obtain the graphene quantum dots;
   5) Preparing the graphene quantum dots into a third solution with a predetermined concentration, wherein the graphene quantum dots are pure, and then adding a predetermined amount of a gadolinium chloride solution to perform a chelation reaction under predetermined conditions to obtain a solution after the chelation reaction; and
   6) Performing a purification and a drying on the solution after the chelation reaction to obtain the graphene quantum dots-gadolinium ion chelate.

2. The method according to claim 1, wherein an ultrasonic power in step 2) is 500-800 W.

3. The method according to claim 1, wherein in step 2), a mass ratio of the graphene oxide to the strong oxidant is (1-3):(1,000-3,000); and
a mass ratio of the graphene oxide to the deionized water is (1-3):(1,000-3,000).

4. The method according to claim 1, wherein the basic compound in step 3) is a mixture of at least one of potassium hydroxide, sodium hydroxide, ammonia, hydrazine hydrate, ethylenediamine, and hydroxylamine.

5. The method according to claim 1, wherein each of the purification in step 4) and the purification in step 6) is at least one selected from the group consisting of suction filtration, chromatography, dialysis, filtration, extraction, distillation, and fractionation;
each of the drying in step 4) and the drying in step 6) is at least one selected from the group consisting of vacuum drying, freeze drying, and high temperature drying.

6. The method according to claim 1, wherein in step 5), the predetermined concentration of the third solution prepared by the graphene quantum dots is 0.05-0.4 mg·mL$^{-1}$; and
a concentration of the gadolinium chloride solution is 0.1-0.5 mmol·L$^{-1}$.

7. The method according to claim 1, wherein the chelation reaction in step 5) is performed by one selected from the group consisting of water bath heating, hydrothermal reaction, solution dialysis, and room temperature treatment.

8. A method of preparing a medical imaging contrast agent, further comprising: using the graphene quantum dots-gadolinium ion chelate prepared by the method according to claim 1.

9. The method according to claim 8, wherein the medical imaging contrast agent comprises a magnetic resonance imaging contrast agent and a fluorescent imaging agent.

10. The method according to claim 8, wherein an ultrasonic power in step 2) is 500-800 W.

11. The method according to claim 8, wherein in step 2), a mass ratio of the graphene oxide to the strong oxidant is (1-3):(1,000-3,000); and
a mass ratio of the graphene oxide to the deionized water is (1-3):(1,000-3,000).

12. The method according to claim 8, wherein the basic compound in step 3) is a mixture of at least one of potassium hydroxide, sodium hydroxide, ammonia, hydrazine hydrate, ethylenediamine, and hydroxylamine.

13. The method according to claim 8, wherein
each of the purification in step 4) and the purification in step 6) is at least one selected from the group consisting of suction filtration, chromatography, dialysis, filtration, extraction, distillation, and fractionation;
each of the drying in step 4) and the drying in step 6) is at least one selected from the group consisting of vacuum drying, freeze drying, and high temperature drying.

14. The method according to claim 8, wherein
in step 5), the predetermined concentration of the third solution prepared by the graphene quantum dots is 0.05-0.4 mg·mL$^{-1}$; and
a concentration of the gadolinium chloride solution is 0.1-0.5 mmol·L$^{-1}$.

15. The method according to claim 8, wherein
the chelation reaction in step 5) is performed by one selected from the group consisting of water bath heating, hydrothermal reaction, solution dialysis, and room temperature treatment.

* * * * *